(12) United States Patent  
Shimasaki et al.

(10) Patent No.: US 7,081,352 B2
(45) Date of Patent: Jul. 25, 2006

(54) CHEMILUMINESCENT INFLUENZA DIAGNOSTIC KIT

(75) Inventors: Craig D. Shimasaki, Edmond, OK (US); Komandoor Elayavalli Achyuthan, Oklahoma City, OK (US); Brooks Edwards, Cambridge, MA (US)

(73) Assignee: Zymetx, Inc., Oklahoma City, OK (US)

( * ) Notice: Subject to any disclaimer, the term of this patent is extended or adjusted under 35 U.S.C. 154(b) by 0 days.

(21) Appl. No.: 10/691,017

(22) Filed: Oct. 22, 2003
(Under 37 CFR 1.47)

(65) Prior Publication Data

US 2004/0086849 A1    May 6, 2004

Related U.S. Application Data

(63) Continuation of application No. 09/548,714, filed on Apr. 13, 2000, now abandoned.

(60) Provisional application No. 60/129,602, filed on Apr. 16, 1999.

(51) Int. Cl.
*C12Q 1/34* (2006.01)

(52) U.S. Cl. ................. 435/18; 435/5; 435/8; 435/975; 536/17.2; 549/510

(58) Field of Classification Search .................. 435/18, 435/5, 8; 536/17.2; 549/510
See application file for complete search history.

(56) References Cited

U.S. PATENT DOCUMENTS

| | | | |
|---|---|---|---|
| 4,331,760 A | 5/1982 | Berger et al. | |
| 4,526,753 A | 7/1985 | Boger et al. | |
| 4,931,223 A | 6/1990 | Bronstein et al. | |
| 4,931,569 A | 6/1990 | Edwards et al. | |
| 4,952,707 A | 8/1990 | Edwards et al. | |
| 4,956,477 A | 9/1990 | Bronstein et al. | |
| 4,978,614 A | 12/1990 | Bronstein | |
| 5,032,381 A | 7/1991 | Bronstein et al. | |
| 5,145,772 A | 9/1992 | Voyta et al. | |
| 5,160,436 A | 11/1992 | Hildenbrand et al. | |
| 5,220,005 A | 6/1993 | Bronstein | |
| 5,225,584 A | 7/1993 | Brooks et al. | |
| 5,252,458 A | 10/1993 | Liav et al. | |
| 5,326,882 A | 7/1994 | Bronstein et al. | |
| 5,330,900 A | 7/1994 | Bronstein et al. | |
| 5,336,596 A | 8/1994 | Bronstein et al. | |
| 5,552,288 A | 9/1996 | Christensen et al. | |
| 5,556,963 A * | 9/1996 | Liav et al. | 536/55.3 |
| 5,663,055 A * | 9/1997 | Turner et al. | 435/18 |
| 5,707,559 A | 1/1998 | Schaap et al. | |
| 5,719,020 A * | 2/1998 | Liav et al. | 435/5 |
| 5,753,436 A | 5/1998 | Bronstein et al. | |
| 5,756,770 A | 5/1998 | Bronstein et al. | |
| 5,763,681 A | 6/1998 | Edwards et al. | |
| 5,773,628 A | 6/1998 | Akhavan-Tafti et al. | |
| 5,777,133 A | 7/1998 | Bronstein et al. | |
| 5,783,381 A | 7/1998 | Bronstein et al. | |
| 5,800,999 A | 9/1998 | Bronstein et al. | |
| 5,827,650 A | 10/1998 | Bronstein et al. | |
| 5,831,102 A | 11/1998 | Bronstein et al. | |
| 5,840,919 A | 11/1998 | Bronstein et al. | |
| 5,843,681 A | 12/1998 | Bronstein et al. | |
| 5,847,161 A | 12/1998 | Bronstein et al. | |
| 5,849,495 A | 12/1998 | Bronstein et al. | |
| 5,851,771 A | 12/1998 | Bronstein et al. | |
| 5,856,522 A | 1/1999 | Bronstein et al. | |
| 5,866,389 A | 2/1999 | Bronstein | |
| 5,869,699 A | 2/1999 | Bronstein et al. | |
| 5,869,705 A | 2/1999 | Bronstein | |
| 5,871,938 A | 2/1999 | Bronstein et al. | |
| 5,891,626 A | 4/1999 | Schaap | |
| 6,555,698 B1 * | 4/2003 | Edwards et al. | 549/510 |

OTHER PUBLICATIONS

Cabezas J. Sialidase Assay by Luminescence in the Low Picomole Range of Sialic Acid. Hoppeseyler's Z Physiol Chem vol. 365, pp. 415-418, Apr. 1984.*

* cited by examiner

*Primary Examiner*—Ralph Gitomer
(74) *Attorney, Agent, or Firm*—Fitch, Even, Tabin & Flannery (57) ABSTRACT

A chemiluminescent system for detecting the presence of influenza virus in a biological fluid sample is provided. An influenza diagnostic kit is provided which includes (1) a sampling device for obtaining the biological fluid from a subject, (2) a chemiluminescent substrate material which, in the presence of influenza virus in the biological sample, will generate a chemiluminescent product that will produce detectable light, and (3) a means for detecting any generated light. A liquid sample containing the biological fluid, and preferably a diluent, are contacted with the an absorbent material containing the chemiluminescent substrate material. The substrate responds to neuraminidase activity intrinsic to influenza A and influenza B virus particles, such that when the substrate is in contact with influenza virus, the substrate is cleaved to yield a chemiluminescent product that then decomposes to produce light which can then be detected. The chemiluminescent substrate materials include enzymatically triggerable 1,2-dioxetane derivatives of 4-alkoxy-N-acetylneuraminic acid and 4,7-dialkoxy-N-acetyineuraminic acid. The system is sufficiently simple that it can reliably be used by a layperson in a nonmedical setting. The biological fluid generally originates from the oral cavity, the pharyngeal cavity, or the nasopharyngeal cavity.

8 Claims, 2 Drawing Sheets

CHEMILUMINESCENT INFLUENZA DIAGNOSTIC KIT

RELATED APPLICATION

This application is a continuation application 09/548,714 filed 4/13/2000, now abandoned, which claim priority to provisional application 60/129,602 filed 4/16/1999.

FIELD OF THE INVENTION

This invention relates to simple and direct systems and methods that permit the detection of influenza virus in a biological sample. The systems and methods of this invention are simple enough that they can reliably be used by non-medical personnel in a nonmedical setting. The invention provides an assay method that is simple, rapid and sensitive for use in detecting viruses, where an enzyme is encoded by the organism. It consists of a specimen collection step, an enzyme specific chemiluminescent substrate, and a high or ultra-high speed film unit for detection of that enzyme action on the specific chemiluminescent substrate. This method is especially adapted for detection and assay for influenza infections and viruses.

BACKGROUND OF THE INVENTION

Viral infections are a principal cause of illness due to communicable diseases that affect the public at large. Of these, influenza viruses, including types A and B, are a significant factor responsible for causing respiratory symptoms as well as systemic malaise; other respiratory viruses include parainfluenza 1, 2, 3, and 4, respiratory syncytial virus, and adenovirus. The influenza viruses undergo rapid mutation of strains, producing pathogens with varying degrees of virulence and severity of symptoms. Recently, influenza infection has been as high as the fifth leading cause of death from acute respiratory disease in the United States (Morbidity and Mortality Weekly Report, 36 (1987) 2).

It is important to have available ways of diagnosing the presence of an influenza infection, and of distinguishing it from related viral and bacterial infections. Particularly among infants, the elderly, and those having compromised or deficient immune responses, early diagnosis of influenza can lead to appropriate treatment to minimize the risk of morbidity and mortality. Diagnosis of viral infection, such as infection by influenza virus, may be carried out by detecting the presence of unique moieties characteristic of the virus. Virus particles typically carry distinctive antigenic components on the exterior of the virion which may be detected by specific ligand-antiligand interactions, in particular by the use of an antibody specific for a viral epitope. Such interactions rely on the law of mass action, and for this reason may have limited sensitivity. Moreover, for viruses that mutate frequently, antibody recognition can be lost, thereby reducing the test's sensitivity and selectivity. Many virus particles additionally carry specific enzymatic activities on the virion particle. Influenza virus is such a virus; it is endowed with a virus-specific neuraminidase activity as an integral part of the virion which is exposed to the environment. Utilization of the enzymatic activity in such cases offers the potential for increasing the sensitivity of a detection method.

N-acetylneuraminic acid (sialic acid, Neu5Ac), whose structure is shown below with the numbering system used herein, is the terminal saccharide residue of many complex carbohydrate side chains of cell surface glycoproteins. In this structure, the C2 position is the anomeric carbon, which is characterized by being part of a hemiketal group or the 2-ketoside moiety. The glycosidic linkage bonding Neu5Ac with the penultimate saccharide is the substrate of the neuraminidase activity of the influenza virion. The neuraminidase hydrolyzes the linkage, thereby cleaving Neu5Ac from the penultimate saccharide. Consequently, suitable synthetic substrates may be derivatives of Neu5Ac in 2-ketoside linkage with a detectable moiety. The moiety then provides a product, when the substrate is acted upon by the viral neuraminidase activity, that signals the presence and amount of influenza virus particles in a sample. Since the viral enzyme cleaves the substrate catalytically, the sensitivity of detecting the presence of the enzyme is greatly enhanced. For this reason the overall sensitivity of detection may be comparable to, and may even be improved over, that provided by antibody binding assays.

One method for detecting the presence of a virus through the reaction of an enzyme with a chromogenic substrate for the enzyme is described in U.S. Pat. No. 5,252,458. Another assay for the direct measurement of influenza neuraminidase was developed by Yolken et al. (J. Infectious Diseases 142 (1980) 516–523). Yolken et al. used the 4-methylumbelliferyl-2-ketoside of Neu5Ac as a fluorescent substrate to measure neuraminidase activity in preparations containing small quantities of cultivated virus as well as in some nasal wash specimens from human volunteers infected with the influenza virus. Yolken et al. suggested that "successful development of influenza neuraminidase might thus provide for a practical means of influenza diagnosis that is sufficiently rapid to allow for the institution of appropriate preventive and therapeutic interventions." According to Yolken et al., calorimetric assays were insufficiently sensitive for clinical applications, suggesting instead that fluorimetric assays for influenza neuraminidase might be suitable for detecting the virus in clinical samples.

Pachucki et al. (J. Clinical Microbiology 26 (1988) 2664–2666) tested the 4-methylumbelliferyl-2-ketoside of Neu5Ac on clinical specimens collected from influenza patients. Due to its low sensitivity, the assay was not useful in detecting neuraminidase in clinical specimens. The assay did, however, identify 91% of virus-positive isolates 25 hours after inoculation of tissue cultures.

The use of modified Neu5Ac substrates can increase the specificity of the neuraminidase assay. In sialic acids, the C4 position has been reported to play an important role in enzyme-substrate interactions. Further, since it is known that salivary bacterial enzymes exhibit neuraminidase activity (Varki et al., J. Biol. Chem. 258 (1983) 12465–12471), it is essential to avoid these undesired enzymatic activities. It has, for example, been shown that ketosides of 4-methoxy-Neu5Ac are resistant towards certain bacterial sialidases (Beau et al., Eur. J. Biochem. 106 (1980) 531–540).

U.S. Pat. No. 5,252,458 to Liav et al. provides a direct chromogenic assay for detecting a virus, including influenza viruses and parainfluenza viruses, that include in the virion a characteristic enzymatic activity, such as neuraminidase activity. The method, which is implemented in a clinic or physician's office, includes incubating a clinical sample suspected of containing the virus with a solution of a chromogenic substrate. The samples typically are obtained by swabbing the pharyngeal, or nasopharyngeal surfaces. If the virus is present, a chromogen is cleaved from the substrate and then reacts with a precipitating agent. The resulting colored precipitate is concentrated for detection (e.g., concentrated as a colored spot on an appropriate substratum). The patent also discloses a kit for use in the clinic or physician's office that includes a filtration device for concentrating the colored precipitate into a spot. This patent provides synthetic routes for the synthesis of a precursor for chromogenic substrates that are useful in the diagnostic assay of viruses. Specifically the patent discloses syntheses for 4-alkoxy-N-acetylneuraminic acid.

U.S. Pat. No. 5,663,055 to Turner et al. discloses 4-modified Neu5Ac chromogenic substrates of viral neuraminidases for use in assays carried out in a clinic or a physician's office. The modification at position 4 includes hydrogen, fluorine, methoxy or ethoxy, and the substrate is sensitive to neuraminidases from influenza and parainfluenza viruses. Clinical samples are used in the assays, and distinct colors are produced as a result. The samples are typically pharyngeal, nasopharyngeal, or respiratory secretions and are collected from patients as, for example, wash, swab, or expectorate specimens.

U.S. Pat. No. 5,719,020 to Liav et al. discloses 4,7-di-O-alkylated chromogenic ketosides of N-acetylneuraminic acid for use as the substrate in assays that are specific for influenza A and influenza B. The assays are also generally performed in a clinic or physician's office. The chromophoric product may be precipitated and the colored precipitate concentrated for detection. Assays are also disclosed that permit discriminating between influenza A and influenza B on the one hand, and other viruses. U.S. Pat. No. 4,331,760 discloses chromogenic sulphonphthalein reagents impregnated in absorbent carriers for the detection of leukocytes in a clinical sample such as urine. The reagents are susceptible to action of esterases present in the leukocytes.

U.S. Pat. No. 4,526,753 discloses a card or strip containing a series of reagent impregnated matrices in sequence, separated by blank spaces, arrayed on a substratum. The strip may be exposed to a sample in order to cause reaction with reagents in the matrices, which may be the same or different.

U.S. Pat. No. 5,552,288 discloses an enzyme linked immunosorbent assay (ELISA) performed on a moist semi-solid sheet comprising chromogen agar paper impregnated with a substrate for an enzyme. Typically the enzyme is the enzyme conjugated to a detecting antibody used in the ELISA. The assay is intended for the detection of any of a variety of serum antibodies to antigens present on pathogens that may infect humans and animals. The assays can be carried out in settings lacking instruments, running water, or other conventional laboratory equipment. In the assay, a sample that may contain the antibody are bound to an immobilized antigen. An enzyme-labeled conjugate is added to bind the antibody. Then a paper coated with a solidified agar containing a substrate for the enzyme is added, and color from the substrate may develop if the assay is positive.

U.S. Pat. No. 5,160,436 discloses a multilayer test device including a permeable support membrane having a macroporous membrane on one side and a microporous membrane on its other side. Upon applying a fluid test sample to the macroporous membrane, free flow of fluid through this membrane and support membrane to the microporous membrane proceeds. This permits separation of incompatible reagents.

Although modification of the 4-position of Neu5Ac provides specificity between certain viral and certain bacterial neuraminidase activities, it is still desirable to obtain substrates which provide enhanced specificity between the various viral neuraminidase reactivities while maintaining the specificity between viral and bacterial neuraminidase activities. Such substrates allow, for example, high specificity for particular types of neuraminidase-containing viruses and allow better and more directed treatment regimes. Use of specific substrates thus allows for more accurate surveillance of viral infections and more focused medical intervention as appropriate. U.S. Pat. No. 5,719,020 provides chromogenic and fluorogenic 4,7-disubstituted N-acetylneuraminic acid substrates for viral neuraminidase activities. These derivatives provide further specificity or differentiation between the various viral neuraminidase activities while maintaining the specificity between viral and bacterial neuraminidase activities. In particular, the 4,7-modified Neu5Ac chromogenic substrates of U.S. Pat. No. 5,719,020 can distinguish between influenza type A and B viruses, on the one hand, and neuraminidases from other viral and bacterial pathogens, on the other. A chromogenic derivative of 4-O-methyl Neu5Ac, however, develops color when exposed to parainfluenza virus types 1 and 2, and mumps, in addition to influenza types A and B.

The synthetic procedures leading to the 4,7-disubstituted chromogenic Neu5Ac ketoside derivatives disclosed in U.S. Pat. No. 5,719,020 have certain difficulties associated with them. These include the provision of synthetic routes involving a large number of distinct chemical reactions. In addition, the 4,7-disubstituted derivatives are the minor component in a mixture of products, requiring extensive purification. These and other factors lead to considerable difficulties and disadvantages related to the synthesis of the 4,7-disubstituted chromogenic Neu5Ac ketoside derivatives. U.S. Pat. No. 5,719,020 addresses these difficulties and provides optimized synthetic procedures providing high yields of the desired pure 4,7-disubstituted chromogenic Neu5Ac ketoside derivatives.

Recently there has been intense interest in biological assay methods employing chemiluminescence using enzymatic triggerable 1,2-dioxetane molecules. Researchers have clearly established 1,2-dioxetanes as chemiluminescence compounds which can be used as reporters in ultrasensitive assays that can be conducted quickly, without resort to exotic conditions or elaborate apparatus, for the detection of a variety of biological materials. Both Tropix, Inc. (New Bedford, Mass.) and Lumigen, Inc. (Detroit, Mich.) have been especially active with regard to chemiluminescence using enzymatic triggerable 1,2-dioxetane. A number of such systems are described in, for example, U.S. Pat. Nos. 4,931,223; 4,931,569; 4,952,707; 4,956,477; 4,978,614; 5,032,381; 5,145,772; 5,220,005; 5,225,584; 5,326,882; 5,330,900; and 5,336,596; 5,707,559; 5,753,436; 5,756,770; 5,763,681; 5,773,628; 5,777,133; 5,783,381; 5,800,999; 5,827,650; 5,831,102; 5,840,919; 5,843,681; 5,847,161; 5,849,495; 5,851,771; 5,856,522; 5,866,389; 5,869,699; 5,869,705; 5,871,938; and 5,891,626, each of which are hereby incorporated by reference. Together, this wealth of patent literature addresses 1,2-dioxetanes stabilized by a typically polycyclic group, preferably spiroadamantane bonded to one of the carbons of the dioxetane ring, and a moiety bonded to the remaining carbon of the dioxetane ring which is electron sensitive, such that deprotection of the electron sensitive moiety, typically an aryl group, more preferably a phenyl or naphthyl group, leads to an anion, generally an oxyanion, which is unstable, and decomposes. Through decomposition, the O—O bond is broken, and a photon is generated. The same carbon atom to which this electron sensitive moiety is bonded may bear an alkoxy or other electron-active group. Methoxy is a preferred moiety. Assays using chemiluminescence derived from enzymatic triggerable 1,2-dioxetane are generally rapid, very sensitive, and convenient. The amount of light generated, or degree of chemiluminescence, can be correlated with the amount of the specific enzyme present. Assays using photographic film to detect and quantify the light generated are possible using such systems.

Nonetheless, methods utilizing the high sensitivity and selectivity of such chemiluminescence systems, including the 1,2-dioxetane chemiluminescence system, have not been used in detecting influenza and related viruses. Thus, it would be desirable to provide a viral analysis, and especially an influenza analysis, using chemiluminescence systems and especially the 1,2-dioxetane system. Moreover, because of the high prevalence of influenza in the population, it would be advantageous to have available an assay that can be carried out conveniently and, if necessary or desired, by a layperson in a nonmedical setting. The assays available at present generally fail to provide such an assay. Generally these assays are sufficiently complex or require such laboratory equipment that they must be conducted in a clinic or a physician's office. There is a need, therefore, to provide a test system, and a diagnostic test kit that is sufficiently simple in operation and other requirements that nonmedical personnel or layperson are able to conduct, for example, an influenza test in a nonmedical setting such as, for example, the home. Such a kit or method would ideally allow such a layperson to directly collect and test the sample from himself or from another individual such as a child, a person in poor health, or an elderly person in an nonmedical setting (e.g., the home, nursing home, and the like). The present invention satisfies these needs and objectives. The present invention can also be used in traditional clinical or medical environments by, if desired, by personnel with limited laboratory training.

SUMMARY OF THE INVENTION

The present invention provides a chemiluminescence system for detecting the presence of influenza virus in a biological sample. Preferably the biological fluid and a diluent composition are mixed to form a liquid sample. The detection portion of the system utilizes a chemiluminescence moiety attached to the 2 position (via an ether linkage) of either a 4-alkoxy-N-acetylneuraminic acid or a 4,7-dialkoxy-N-acetylneuraminic acid. Preferably, the chemiluminescence moiety is an enzymatically triggerable 1,2-dioxetane. More preferably, the chemiluminescence moiety has an adamantyl-stabilized 1,2-dioxetane of general structure attached to the 2-position of the 4-alkoxy-N-acetylneuraminic acid or 4,7-dialkoxy-N-acetylneuraminic acid through an ether linkage.

The substrate responds to neuraminidase activity intrinsic to influenza A and influenza B virus particles. When the substrate is in contact with influenza virus, the chemiluminescence substrate is cleaved to yield, ultimately, a phenoxide anion and emission of light. Preferably, the light is detected by a high or ultra-high speed and high sensitivity photographic film; even more preferably, the photographic film is part of an instant film system in which the film is automatically developed within a few minutes or less. The system is sufficiently unencumbered as to be usable by a layperson in a nonmedical setting. In important embodiments, the biological fluid originates from the oral cavity, the pharyngeal cavity, or the nasopharyngeal cavity. Preferred chemiluminescence substrates or compounds for use in this invention include 1,2-dioxetanes having the following structures:

and where the R groups are independently selected from alkyl radicals having 1 to 6 carbon atoms. Preferably, the R groups are independently selected from alkyl radicals having 1 to 4 carbon atoms (i.e., methyl, ethyl, propyl, isopropyl, and normal and branched butyl radicals). More preferably, each R group is a methyl radical. Generally, the 4,7-dimethoxy-N-acetylneuraminic acid-containing substrates are preferred because of their higher selectivity with respect to influenza A and B.

The chemiluminescence substrate can be included in a kit-designed to be used by laypersons in a nonmedical setting. Such a kit could, for example, include a sampling device comprising a porous sheet, film, fibrous material, or the like which contains the chemiluminescence substrate. Preferably, the sampling device is an integral part of the test device and is backed with a high or ultra-high speed photographic film (preferably an instant type film) for detection. In such a kit, the biological sample would be applied to the porous sheet or other sample collection material. If influenza A or B is contained within the sample, it will react with the chemiluminescence substrate thereby producing light. The light generated would be recorded by the high or ultra-speed photographic film. After a predetermined time, the photographic film could be developed and then examined for the presence of light generated by the chemiluminescence substrate. Of course, the porous sheet should be opaque or be covered with an opaque covering to prevent light other than from the decomposition of chemiluminescence substrate from reaching the photographic film. Using an instant type high or ultra-speed film for detection would allow the influenza test to be carried out by a layperson in a nonmedical setting. Non-instant type film would, of course, require development of the film using conventional film processing techniques. Preferably, a high or ultra-high speed (2000 ASA or higher) instant developing type film is used to detect any light generated by the chemiluminescence substrate.

Alternatively, the device could contain a sample entry port and a separate light tight compartment containing the chemiluminescence substrate and the high or ultra-speed film. The biological sample, once placed in the entry port and on appropriate absorbent material, could be physically moved or transferred into the light tight compartment and into contact with the chemiluminescence substrate. Such movement or transfer could be carried out by a mechanical device (e.g., a mechanical lever) or a battery-operated transfer device. Both the reaction with the chemiluminescence substrate and the exposure of the film to any light generated from the 1,2-dioxetane would occur in the light tight compartment. After introducing the biological sample into the light tight compartment and contacting the chemiluminescence substrate for the appropriate amount of time, the film can be removed and read. Preferably, the high or ultra-speed film is the instant-type film (i.e., one having all necessary development components within the film package or cassette itself) and which can be read with a few minutes after exposure.

The kit could also include a sampling device encompassing means to obtain a biological fluid from the subject. Thus, a biological fluid containing droplets suspended in exhaled air could be directed, via a mouthpiece, towards the absorbent material containing the chemiluminescence substrate or into the sample entry port. Such a device could be mountable over the mouth and nose such that droplets are entrapped on the absorbent material when the subject wearing the device mounted over the mouth and nose projects exhaled air onto the sheet. Of course, other sample handling systems could be used so long as the biological sample can be introduced into the sampling device.

The invention provides a method of detecting influenza virus in a subject suspected of being infected with influenza. The method includes the steps of (1) obtaining a biological fluid from the subject;
(2) contacting at least a portion of the biological fluid with a substrate containing a chemiluminescent derivative of 4-alkoxy-N-acetylneuraminic acid or a chemiluminescent derivative of 4,7-dialkoxy-N-acetylneuraminic acid such that, when the substrate is in contact with influenza virus contained in the fluid, it yields a chemiluminescence product which generates light; and
(3) detecting whether light has been generated.

Preferably, the chemiluminescent derivative is a 1,2-dioxetane which is coupled with N-acetylneuraminic acid at the 2-position via an ether linkage. Preferably, the biological fluid is obtained from the oral cavity, the pharyngeal cavity, or the nasopharyngeal cavity, and the chemiluminescent derivative is a 1,2-dioxetane derivative of 4,7-dialkoxy-N-acetylneuraminic acid. Even more preferably, the chemiluminescent derivative is a 1,2-dioxetane derivative of 4,7-dimethoxy-N-acetylneuraminic acid.

DETAILED DESCRIPTION OF THE INVENTION

The present invention provides a chemiluminescence system for detecting the presence of influenza virus in a sample. The sample (normally liquid) contains the biological fluid and a diluent composition, and the system includes a 1,2-dioxetane moiety attached to a 4-alkoxy-N-acetylneuraminic acid or a 4,7-dialkoxyl-N-acetylneuraminic acid as the chemiluminescence substrate. The substrate responds to neuraminidase activity intrinsic to influenza A and influenza B virus particles. When the substrate is in contact with influenza virus, the chemiluminescence substrate is cleaved to yield a N-acetylneuraminic acid and an unstable 1,2-dioxetane which then decomposes, generally under basic condition, to a phenoxide anion with the emission of light. Preferably, the light is detected by a high or ultra-high speed, high sensitivity photographic film; even more preferably, the photographic film is part of an instant film system in which the film is automatically developed within a few minutes or less. The system is sufficiently unencumbered as to be usable by a layperson in a nonmedical setting. In important embodiments, the biological fluid originates from the oral cavity, the pharyngeal cavity, or the nasopharyngeal cavity.

In practice, a specimen is taken from an individual suspected of having a viral infection such as influenza. The specimen source could be a throat swab in the case of respiratory viral infections such as influenza, parainfluenza, adenovirus or bacterial infections such as streptococcus; a nasal wash, a nasal aspirate, a bodily fluid such as blood, urine, or cerebral spinal fluid. The specimen to be tested would preferably be placed into a container or tube containing a small amount of extraction buffer or emulsifier to liberate or facilitate the enzyme activity associated with the organism of detection. Additional excipients can also be added to provide buffering and enhancement or increased enzyme activity. The extracted specimen is then contacted with the enzyme specific chemiluminescent material on a suitable substrate which is, or will be, in optical contact with a high or ultra-high speed film. Generally, the system is incubated between ambient temperature and body temperature for about 1 to 60 minutes (preferably for about 10 minutes), preferably filtered, and then activated (generally by raising the pH to about 8 or higher, preferably to about 8 to 12, and most preferably to about 10). Under basic conditions, the 1,2-dioxetane will decompose with the emission of light. The photons of light liberated by enzymatic action on the chemiluminescent substrate produces a spot, mark, or imprint on the high or ultra-high speed film indicating the organism was present in the sample. The amount of light impinging on the film during the assay can be used to estimate or quantify the amount of viral infectious agent present. If desired, a simple lens can be mounted between the chemiluminescent material and the film to focus any light generated on a smaller area of the film in order to increase the sensitivity of the test. The specimen is allowed to interact with the chemiluminescent substrate for a short period of time, typically 5 minutes to 1 hour. The enzyme interaction produces an activated or liberated chemiluminescent molecule such that addition or contact with an accelerator would liberate photons of light. Of course, the film must be protected from ambient or extraneous light so that the only light energy reaching the film will be from the chemiluminescent reaction associated with the viral infection of interest.

The chemiluminescent substrates or compounds used in the present invention are prepared by coupling a 1,2-dioxetane reporter molecule to a 4-alkoxy-N-acetylneuraminic acid or a 4,7-dialkoxy-N-acetylneuraminic acid. The chemiluminescent substrates or compounds are preferably purified prior to their use in the present invention. The 1,2-dioxetane repoter molecule coupled to the 4-alkoxy-N-acetylneuraminic acid can be used to detect viruses associated with influenza A, influenza B, parainfluenza, and mumps. The 1,2-dioxetane repoter molecule coupled to the 4,7-dialkoxy-N-acetylneuraminic acid offers more selectivity since it only detects influenza A and B. If desired, the two different chemiluminescence substrates can be included in single assay to obtain even more information regarding a patient. Thus, a positive reaction with both chemiluminescence substrates suggests the presence of influenza A or B, parainfluenza, or mumps. A positive reaction with only the 4,7-modified chemiluminescence substrate suggests the presence of influenza A or B.

In either case, the substrate can react with neuraminidase enzyme activity to liberate a 1,2-dioxetane that is unstable under alkaline conditions. Decomposition of 1,2-dioxetane leads to the generation of a phenoxide anion and emission of light. The emitted light strikes a highly sensitive photographic film to produce a white spot (or other shaped area) against a black background indicating the presence of (1) influenza A or influenza B virus in the sample specimen in the case of the 4,7-dialkoxyl-N-acetylneuraminic acid-containing chemiluminescent substrate or (2) influenza A, influenza B, parainfluenza, or mumps in the case of the 4-alkoxy-N-acetylneuraminic acid-containing chemiluminescent substrate. Alternately, the emitted light could be detected using a light-detecting instrument such as a photomultiplier tube luminometer, photodiode apparatus, liquid scintilliation counter, or like systems.

Figure 1:
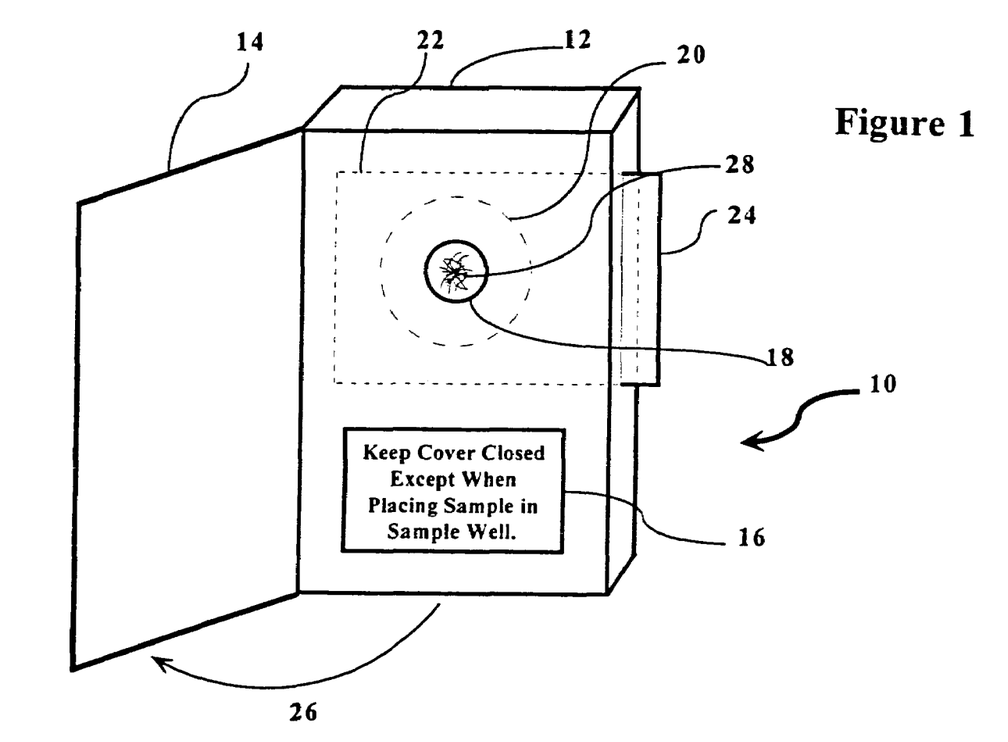
FIG. 1 illustrates one embodiment of the assay system of the present invention.

One embodiment of a device suitable for use in such an assay is provided in FIG. 1. As shown, device 10 comprises a light tight box or container 12 having a front flap 14 which can open or close on box 12 as indicated by arrow 26. In the closed position, it provides additional protection against ambient light. The front surface of box 12 has a sample entry port 18 to receive the biological sample. The sample port contains an absorbent material 28 containing the chemiluminescent substrate and placed in the bottom of entry port 18. Located within the light tight box and adjacent to the chemiluminescent substrate on absorbent 28 is instant film cassette 22. The area 20 of film cassette 22 will collect light from activated or liberated chemiluminescent molecules formed in the presence of neuraminidase enzyme activity. After a predetermined time (during which time the front panel 14 should be closed to reduce effects of ambient light), the film 22 is removed from the box 12 using strip 24. Pulling the film 22 out of the box should initiate development of the instant film. After the film is developed, area 20 is examined to determine if any light was generated. A white or lighter spot or other markings on area 20 indicates the presence of the influenza virus. Panel 16 can be used to provide appropriate warnings or other instructions. Instructions can also be placed on either side of cover 14 or simply included with the assay kit.

Figure 2:
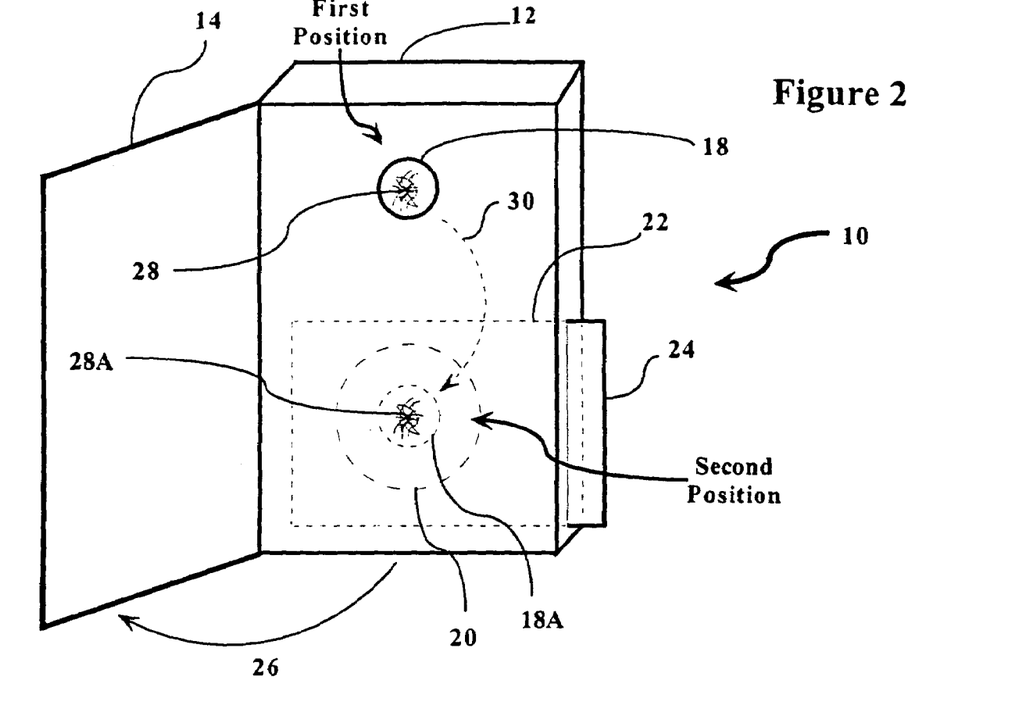
FIG. 2 illustrates another embodiment of the assay system of the present invention.

Another embodiment of device 10 is shown in FIG. 2 (like numbers in the Figures refer to similar components). In this embodiment, the film 22 and the sample entry port 18 are located in different parts of the box 10 to help insure that ambient light will not strike and cloud the film. Once the biological sample is placed in the sample entry port 18 (Position 1) and its contents 28 (substrate and biological sample) are rotated or moved using any suitable leaver, other mechanical device, or battery-driven devce (not shown) to Position 2, thereby bringing the substrate and biological sample adjacent to, and in optical communication with, film 22. The path of movement from Position 1 to Position 2 is indicated by arrow 30. During this movement, the sample 28 enters and remains within the light tight compartment containing film 22. If desired, a movable shutter or flap could be used to cover the sample entry port 18 (i.e., Position 1) at all times except during actual sampling. Except for the shifting of the unknown sample and the chemiluminescent substrate, the systems works essentially as that described for the device in FIG. 1.

Figure 3:
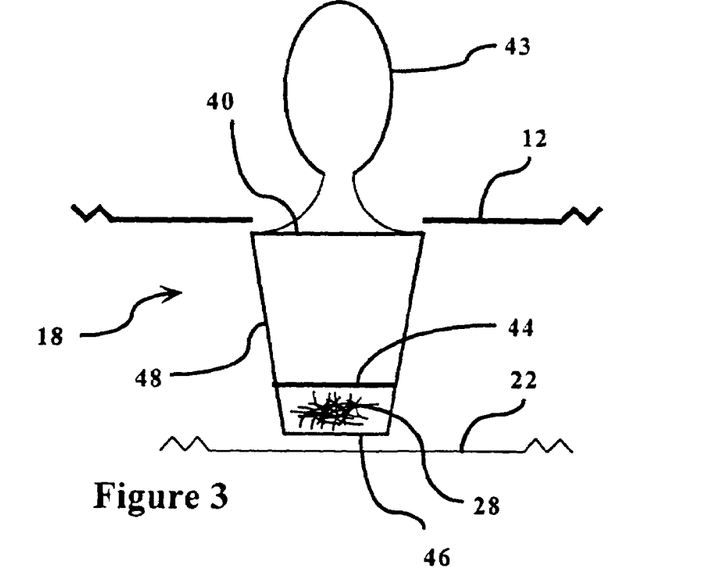
FIG. 3 illustrates a sampling handling system which can be used with the assay system of the present invention.

FIG. 3 illustrates a possible sample handling device for use in the present invention in conjunction with either device shown in FIGS. 1 and 2. Sample entry port 18 is shown in relation to the flat front surface of box 12. Sample entry port 18 is generally in the shape of a funnel or truncated cone. The absorbent material 28 containing the chemiluminescent substrate is located at the bottom of sample entry port 18. A filter 44 is located above absorbent material 28. The sample entry port 18 has a top surface 40, a bottom surface 46, and a side surface 48. In FIG. 3, the top surface 40 (and preferably a portion of the top portion of the truncated cone forming the port 18) can act to receive a bulb 42. In practice, the biological sample is placed within the truncated cone formed by side surface 48 and atop filter 44. Bulb 42 can then be placed over the top 40 of port 18 so as to create at least a partial seal with port 18. The bulb 42 can then be manually squeezed to provide slight air pressure to help force the biological sample through filter 44 and onto the absorbent material 28. Such a bulb 42 can be included in a kit containing the device. Alternatively, gravity flow or other flow-assisted methods can be used to introduce the biological sample into the test device. Preferably, the filter 44 is at least partially opaque so as to prevent ambient light from entering the system. Likewise, the side surfaces 48 should also be opaque. The bottom 46 of the sample entry port must, of course, be at least semi-transparent and preferably transparent to allow any light generated from the chemiluminescent substrate to pass through for detection by the photographic film. Transparent glass or plastic can be used to form bottom 46. Thus, the bottom 46 should be in close proximity to the film 22 using the system from FIG. 1 or be movable to be in close proximity to the film 22 using the system from FIG. 2. Although FIG. 3 illustrate a sample handling system which is incorporated into box 12, other sampling handling systems could be employed wherein similar steps are taken outside the box 12.

Modifications to further improve the sensitivity of the chemiluminescent test involving 1,2-dioxetane would include but are not limited to, additions of compounds that would partition the water molecule away from the reporter, separating the 1,2-dioxetane free of other reactant components, embedding the reaction products onto hydrophobic membranes, additions of other fluorescers or other energy accepting molecules to allow for efficient energy transfer and absorbing the product on highly basic solid matrices. Adjustments to pH and other ionic, nonionic or hydrophobic detergent additions to reactions catalyzed by the enzyme would also improve the sensitivity even further. Improvements in chemiluminescent detection may be made by specimen manipulations. These include detergent treatment, filtration, extraction, additions of antioxidants to eliminate or overcome chemiluminescent quenchers that might be present in throat swab, mucus, sputum, blood, urine or stool specimens. Light emission may also be recorded on hand-held light-monitoring devices and allow field testings.

Other chemiluminescent molecules can also be used in the methods and devices of this invention. One substrate synthesized by coupling an aminophthalhydrazide to a sialic acid sugar molecule yielded a compound, the cleavage of which by influenza A neuraminidase could be detected. N-substituted aminophlthalydrazides as well as unsubstituted aminophlthalydrazides could also be used to couple to potential recognition molecules for various enzymes such as hydrolases, esterases, proteases, and neuraminidases. Enzyme-catalyzed hydrolysis of such molecules would result in the liberation of the free reporter. This would then be detected in an oxidative process.

Coupled enzyme assays may also be employed for the chemiluminescent detection of neuraminidase or other enzymes activity in various organisms. An example would be luciferyl-O-Neu5Ac. Neuraminidase-catalyzed hydrolysis would result in the liberation of luciferin. Luciferin can then be detected from the light emission by the action of luciferase. Another example is the chemiluminescent quantization by the hydrolysis of bromo-indolyl-O-Neu5Ac by neuraminidase. A product of this reaction is hydrogen peroxide. The liberated hydrogen peroxide can act upon unsubstituted or N-substituted aminophlthalydrazides in the presence or absence of an oxidative enzyme such as catalase or peroxidase leading to light emission. The bromo-indole itself is a chemiluminescent molecule and thus can be detected by oxidative light emission. Chemical oxidation can involve a variety of oxidizers including but not limited to peroxide, periodic acid, persulfate, permanganate, and ferricyanide plus peroxide combinations. Addition of energy accepting molecules to such systems would further improve light emission and increase sensitivity of film or machine-based detection of organisms.

Yet another example would be the N- or O-coupling of acridinium esters to suitable recognition molecules for various enzymes. Hydrolysis of such potential substrates by various enzymes present in different organisms would liberate the free acridinium ester. The liberated reporter could then be detected by an oxidative process involving intramolecular election transfer. Light emitted from such a chemiluminescent reaction step could be detected by film or light monitoring instrument-based techniques as described above.

The present invention presents a system and diagnostic kit directed to assay for infection by influenza A or influenza B virus. A method of conducting the assay is also included as an aspect of the invention. A significant aspect of the invention is simplification of the components of the test system and kit, and thereby minimization of the steps involved in carrying out the test. As a consequence, a layperson in a nonmedical setting may easily and conveniently carry out the test and determine, by simple visual inspection of the processed film from the test system, whether the biological sample contains influenza A virus or influenza B virus. Because of this ease and convenience of use, a layperson who thinks he or she may be infected with influenza may conduct the test on himself or herself. Correspondingly, a layperson caring for another, such as a child, an ill or incapacitated person, or an elderly person, can just as easily carry out the test on that other person. As used herein, the phrase "employable by a layperson in a non-medical setting", or similar phrases relate to the devices and method of the invention which, as just explained, are for use by persons not trained in clinical, medical, or laboratory practice, and are usable in settings other than a hospital, clinic, medical office, or similar medical facility. In particular, they may be employed in the home. Of course, these kits and methods can be used by medical personnel in a conventional clinical or medical setting.

This invention describes an assay system, a diagnostic kit for use in the home, and a method of carrying out the test using the test system or the kit, for the detection of influenza A virus or influenza B virus. The invention employs 1,2-dioxetanes coupled to 4-alkoxy and/or 4,7-dialkoxy derivatives of Neu5Ac which are substrates of the neuraminidase activity known to be present on the virion surface. The use of these substrates in the test system provides a chemiluminescent product can be detected when the virus, and its accompanying neuraminidase, is present in a biological sample being tested. Preferably, a high or ultra-high speed (e.g., 2000 ASA) instant-type film is used to detect light produced. In general, the chemiluminescent substrates, which contain the 1,2-dioxetane moiety by ketosidic linkage with the Neu5Ac derivative, interact poorly with light so that they neither absorb nor emit light to a significant extent. However, when acted upon by the viral neuraminidase, the chemiluminescent substrate liberates an unstable or meta-stable 1,2-dioxetane intermediate which leads to the generation of a phenoxide anion and emission of light. As used herein, the terms "detectable" and "visibly detectable" and synonymous terms relate to the property that the liberated chemiluminescent moiety provides light in the wavelengths of the visible spectrum detectable using by conventional optical or instrumental means of detection or enhancement.

The substrates that are employed in the present invention are characterized generally by the formula wherein $R_1$ and $R_2$ generally are the same or different and are alkyl radicals containing 1 to 6 carbon atoms and wherein Y is the chemiluminescent moiety. Preferably, $R_1$ and $R_2$ are independently methyl, ethyl, propyl, isopropyl, and normal or branched butyl groups. Most preferably, both $R_1$ and $R_2$ are methyl. The chemiluminescent moiety Y is linked to the Neu5Ac portion at the 2-position and in the α-anomeric configuration. Preferably, Y is a stabilized 1,2-dioxetane moiety such that, when cleaved by the action of a neuraminidase, the 1,2-dioxetane moiety is released and, in turn, decomposes to unstable phenoxy ion with generation of light (i.e., chemiluminescent).

A diluent may be mixed with the biological fluid to be tested either before or during the actual analysis. Such diluents may contain by way of nonlimiting example, components such as biologically compatible salts, buffering substances, detergents or surfactants, and stabilizers. The diluent preferably contains a buffer that maintains the pH at about 4 to about 7, preferably about 5.5 to about 6.5, optionally about 0.1% to about 10 % by weight nonionic detergent, a small amount (about 1–20 mM) of alkaline earth metal cation ($Ca^{+2}$, $Mg^{+2}$, preferably $Ca^{+2}$), and a sufficient amount of a stabilizer selected from the group consisting of alditols, monosaccharides, and disaccharides to enhance the thermal stability of the chromogenic substrate in the sample.

The volume of diluent solution combined with the specimen will normally be about 0.1 to about 2 mL. The buffer included in the diluent may be organic or inorganic. Suitable buffers include, for example, conventional buffers of organic acids and salts thereof such as citrate buffers (e.g., monosodium citrate-disodium citrate mixture, citric acid-trisodium citrate mixture, citric acid-monosodium citrate mixture, etc.), acetate buffers (e.g., acetic acid-sodium acetate mixture), succinate buffers (e.g., succinic acid-monosodium succinate mixture, succinic acid-sodium hydroxide mixture, succinic acid-disodium succinate mixture, etc.), tartrate buffers (e.g., tartaric acid-tartrate mixture, tartaric acid-potassium tartrate mixture, tartaric acid-sodium hydroxide mixture etc.), fumarate buffers (e.g., fumaric acid-monosodium fumarate mixture, fumaric acid-disodium fumarate mixture, monosodium fumarate acid-disodium fumarate mixture), gluconate buffers (e.g., gluconic acid-sodium gluconate mixture, gluconic acid-sodium hydroxide mixture, gluconic acid-potassium gluconate mixture, etc.) oxalate buffers (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate-mixture, etc.), acetate buffers (e.g., acetic acid-sodium acetate mixture, acetic acid-sodium hydroxide mixture, etc.), malate buffers (e.g., D,L-malic acid-disodium malate mixture), phosphate buffers (e.g., monosodium phosphate-disodium phosphate mixture, monosodium phosphate-sodium hydroxide mixture, trisodium phosphate-hydrochloric acid mixture, etc.), 2-(N-morpholino)ethanesulfonic acid, [bis-(2-hydroxyethyl)imino]tris(hydroxymethyl)methane, -2-acetamidoiminodiacetic acid, 1,3-bis[tris(hydroxymethyl)methylamino]propane, piperazine-N,N'-2-ethanesulfonic acid), N-2-acetamido-2-aminoethanesulfonic acid, 3-(N-morpholino)-2-hydroxypropanesulfonic acid, 3-(N-morpholino)propane acid, 2-[tris(hydroxy-methyl)methylamino]ethanesulfonic acid, N-2-hydroxy-ethylpiperazine-NN'-2-ethanesulfonic acid, a 3-[tris-(hydroxymethyl)methylamino]-2-hydroxypropanesulfonic acid.

Non-ionic detergents may be used in the diluent, and include, for example, Pluronics, such as Polysorbate 20 or Polysorbate 80, Triton X-100, NP-40, and alkyl glucosides such as $C_8$ and $C_9$ alkyl glucosides. The detergent is an optional component and facilitates release of the neuraminidase from the viral envelope. Stabilizers may also be used in the diluent, and include, for example, trihydric or higher alditols, such as glycerin, erythritol, arabitol, xylitol, sorbitol, mannitol, the hexoses glucose and fructose and the disaccharide sucrose. These stabilizers can be used alone or in combination. In order to stabilize the activity of the neuraminidase-containing viruses, the stabilizers are added to the liquid formulation/excipient system in an amount from about 0.2 M to about 2.1 M and preferably about 0.6 M to about 2.0 M.

The diluent may be applied in any manner-that is effective to allow the biological fluid to contact the chemiluminescent substrate. This includes, by way of nonlimiting example, spraying, direct application of liquid, or immersion of absorbent material containing the chemiluminescent substrate in a container holding the diluent. For example, the diluent may be contained in a separate compartment which is pierced or otherwise opened only when the biological fluid is introduced into the light tight boxes illustrated in FIGS. 1 and 2. Thus, when the biological fluid is added via the sample entry port 18 in FIGS. 1 or 2, a compartment (not shown) containing the diluent could deliver the diluent to the area of the entry port to mix with the biological sample and be carried to contact the chemiluminescent substrate material. Likewise, at the same time as the addition of the biological fluid, a cover or shutter-type mechanism (not shown) could also be activated to bring the chemiluminescent substrate in optical communication with the film 22 in the event that light is generated.

Likewise and if desired, a control assay (not shown) could be incorporated into the devices of FIGS. 1 and 2. Such a control assay could be activated, for example, at the same time as the biological fluid is introduced by mixing a second diluent sample containing neuraminidase enzyme to a second sample of chemiluminescent substrate material such that, if the system is working properly, a light spot will be developed on the film in an area removed from the area associated with the unknown sample (area 20 in FIG. 1). This second area will indicate a positive result (i.e., a light spot or other image) if the kit is working properly. Failure to obtain the control positive would indicate that the assay is not working properly. The area associated with the unknown sample will, of course, be used to confirm the presence or absence to the viral agents.

The absorbent material 28 used in the sample entry port 18 to contain the chemiluminescent substrate may be in the form of porous and/or absorbent sheets or fibrous materials. A wide range of suitable synthetic and natural materials exists. Synthetic materials include sheets or membranes prepared from polymeric, or crosslinked polymeric, materials. By way of nonlimiting example, synthetic polymers that may be incorporated into the sheets or fibrous materials include polyvinyl polymers and derivatives thereof such as polyethylenes, polypropylenes, polyacrylates and derivatives thereof, polymethacrylates and derivatives thereof, polyacrylamides, halogenated polyvinyl polymers, polystyrene, and the like. Synthetic polymers may also include polyesters, polyamides, polyethers, polysulfones, and the like. The porous sheets or fibrous materials may also be fabricated from glass fibers, including glass fibers modified by derivatization of the silicate groups. The sheets or fibrous materials may further be composed of natural fibers and derivatives thereof, where such materials include cellulose, cellulose derivatives such as nitrocellulose, alkylated cellulose derivatives, carboxylated cellulose derivatives, aminated cellulose derivatives, cellulose esters, and comparable materials with equivalent porous and convection enhancing properties. Other materials generally equivalent to those enumerated herein are also envisioned within the scope of the invention.

The enzymatic activity of any influenza viral neuraminidase that may be present in the biological sample applied to be tested can be enhanced as the temperature is raised, provided the temperature remains below a temperature at which the neuraminidase becomes inactivated. In the method of this invention, therefore, it is advantageous to increase the temperature at which the enzyme is kept in contact with the substrate above ambient temperature. Accordingly, a means for incubating the test system at an elevated temperature (i.e., about body temperature) can be included in the kit or method intended to be used in the home. This means does not require any laboratory or other conventional apparatus or equipment to maintain the temperature at such an elevated temperature. Specifically, the elevated temperature can be provided by the human body, such as the body of the subject being tested. An adhesive agent or other means can be used to reversibly fix the testing device to the body. Generally, the time required is short so that, if desired, the testing device can simply be held against the body. Of course, incubation temperatures below body temperature (and preferably about or greater than about 20–25° C.) can be used; in such cases, however, longer incubation times may be required. Indeed, because of convenience to the user, incubation at ambient temperatures will often be preferred. Once the sample has under gone incubation, the pH of the system can be raised to initiate the chemiluminescent reactions.

The diagnostic kit of the present invention includes the test system described in detail above. It may also include a sampling device that includes means to obtain a biological fluid from a subject and means to prepare a liquid sample therefrom for application to the test system. In general, the sampling device of the invention is preferably administrable by a layperson in a nonmedical setting, comprising means to obtain the biological fluid from the subject. The biological fluids that are tested in the invention will typically be pharyngeal, nasopharyngeal, or respiratory secretions collected from patients suffering, or suspected of suffering, from influenza as wash, swab, or expectorate specimens. The wash, expectorate, or swab will preferably be combined with an aqueous buffer solution (i.e., diluent) prior to use in the present method.

A variety of procedures of obtaining the biological fluid and preparing the liquid sample are possible and may be applied in the method of the present invention. For example, the subject may be instructed to cough once or twice. Then a sterile swab is used to sample the oral cavity, the pharyngeal cavity, or the nasopharyngeal cavity for salivary and mucous fluids contained therein, and that may include fluid or airborne components expelled from the respiratory system upon coughing. The swab may be introduced into a portion of a sterile liquid, such as water or the diluent of the invention, to suspend any viral particles adhering to the swab in the liquid. The sterile liquid is preferably supplied with its container as a component of the diagnostic kit. A fixed volume, such as about 2–3 drops, of the resulting liquid sample is then applied to the chemiluminescent substrate.

In another example, the sampling device can include the absorbent material containing the chemiluminescent substrate affixed in a mask or comparable holder that is mountable over the mouth and/or nose. With such an arrangement, the absorbent material entraps any droplets including the biological fluid that may be suspended in exhaled air, when the subject wearing the mask or holder mounted over the mouth and nose coughs or exhales air forcefully onto the absorbent material. In other words, the subject would deposit the biological sample directly onto the absorbent material. The absorbent material could then be transferred to the device for analysis. Alternatively, the sample can be collected on a swab and directly transferred to the device or transfered first to a diluent solution and then to the device. Other equivalent arrangements of the components of the sampling device, the test system, and the procedures to be employed are envisioned Within the scope of the invention. Such equivalents will be apparent to a skilled artisan in the practice of diagnostic tests upon a consideration of the present specification.

All patents and literature references included in, or referred to by, this specification are hereby incorporated by reference.

EXAMPLE

Throat swab specimens were collected using a foam swab from patients complaining of flu-like symptoms. The foam swab was then extracted into a buffered solution at pH 5.4 containing a detergent. The detergent extract of the patient specimen was then filtered through a 10 µ filter. The filtrate was collected into amber vials containing the 1,2-dioxetane 4,7-dialkoxy-N-acetylneuraminic acid and then incubated at ambient temperature for 10 minutes. The reaction was terminated by adding a highly alkaline solution containing hydrophobic compounds and fluorescer molecules. This mixture was then transferred rapidly to a plastic manifold cell seated above a sensitive photographic film inside a light-tight chamber. Light from the released product undergoing decomposition strikes the photographic film to produce a white spot for image against a black background indicating the presence of either influenza A or influenza B virus in the patient specimen. Alternately, the emitted light from the decomposing 1,2-dioxetane product could be measured using a photomultiplier luminometer, a photodiode apparatus or a liquid scintillation counter.

This assay was applied to a group of 27 patients complaining of flu-like symptoms who visited a local clinic. The chemiluminescent film-format test described herein correctly identified the patients with the flu with a sensitivity of 88% and a specificity of 100%.

We claim:

1. An influenza diagnostic kit comprising:
   (1) a sampling device to obtain a biological fluid sample from a subject;
   (2) (i) a substrate containing a chemiluminescent derivative having a formula wherein each R is independently selected from the group consisting of alkyl radicals having 1 to 6 carbon atoms, such that when the chemiluminescent derivative is in contact with influenza virus contained in the fluid sample, it will yield a chemiluminescent product which will generate light, and (ii) a photographic film in optical communication with the chemiluminescent derivative to detect the light if generated; wherein the kit can be used by a layperson in a nonmedical setting.

2. The influenza diagnostic kit as described in claim 1, wherein each R is methyl.

3. The influenza diagnostic kit as described in claim 2, wherein the photographic film is an instant type film.

4. The influenza diagnostic kit as described in claim 1, wherein the fluid sample is mixed with a diluent prior to contacting the chemiluminescent derivative.

5. The influenza diagnostic kit as described in claim 2, wherein the fluid sample is mixed with a diluent prior to contacting the chemiluminescent derivative.

6. The influenza diagnostic kit as described in claim 3, wherein the fluid sample is mixed with a diluent prior to contacting the chemiluminescent derivative.

7. The influenza diagnostic kit as described in claim 1, wherein the biological fluid sample is obtained from an oral cavity, a pharyngeal cavity, or a nasopharyngeal cavity.

8. The influenza diagnostic kit as described in claim 6, wherein the biological fluid sample is obtained from an oral cavity, a pharyngeal cavity, or a nasopharyngeal cavity.

* * * * *